(12) United States Patent
Hawkins et al.

(10) Patent No.: US 10,370,625 B2
(45) Date of Patent: *Aug. 6, 2019

(54) CLEANING COMPOSITION, METHOD OF MAKING AND USE THEREOF

(71) Applicants: MOREHOUSE SCHOOL OF MEDICINE, Atlanta, GA (US); DEVMAR PRODUCTS, LLC, Nashville, TN (US); INNOVATIVE ENVIRONMENTAL COMPANIES, Rockford, IL (US)

(72) Inventors: Walter Hawkins, Delafield, WI (US); Sharon W. Reynolds, Brentwood, TN (US); James W. Lillard, Jr., Smyrna, GA (US); Qing He, Conyers, GA (US); Harry Michael Jones, Jonesboro, GA (US)

(73) Assignees: MOREHOUSE SCHOOL OF MEDICINE, Atlanta, GA (US); DEVMAR PRODUCTS, LLC, Nashville, TN (US); INNOVATIVE ENVIRONMENTAL COMPANIES, Rockford, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/696,480

(22) Filed: Sep. 6, 2017

(65) Prior Publication Data
US 2018/0066216 A1    Mar. 8, 2018

Related U.S. Application Data

(60) Provisional application No. 62/495,274, filed on Sep. 8, 2016.

(51) Int. Cl.
| | |
|---|---|
| *C11D 3/48* | (2006.01) |
| *A01N 25/26* | (2006.01) |
| *C11D 11/00* | (2006.01) |
| *C11D 17/00* | (2006.01) |

(52) U.S. Cl.
CPC .......... *C11D 17/0039* (2013.01); *A01N 25/26* (2013.01); *C11D 3/48* (2013.01); *C11D 11/0088* (2013.01)

(58) Field of Classification Search
CPC ... C11D 17/0039; C11D 11/0088; C11D 3/48; A01N 25/26
See application file for complete search history.

(56) References Cited

U.S. PATENT DOCUMENTS

| 4,497,869 A * | 2/1985 | Kamigaito ............ C04B 14/206 241/21 |
| 6,905,698 B1 | 6/2005 | Aldcroft et al. |
| 8,758,503 B2 | 6/2014 | Anderson et al. |
| 2003/0143187 A1* | 7/2003 | Worley .................. A01N 59/00 424/78.22 |
| 2007/0065475 A1 | 3/2007 | Elfersy |
| 2007/0179079 A1 | 8/2007 | Kilkenny et al. |
| 2012/0308626 A1 | 12/2012 | Wang |
| 2014/0326192 A1 | 11/2014 | Coupe et al. |
| 2018/0265822 A1* | 9/2018 | Hawkins ............. C11D 11/0088 |
| 2019/0017000 A1* | 1/2019 | Hawkins ............ C11D 17/0039 |

FOREIGN PATENT DOCUMENTS

WO    WO-2014149052 A1 *    9/2014    ............ C04B 26/06

OTHER PUBLICATIONS

"Perlite as an absorbent or carrier," Perlite Institute, Inc., pp. 1-2, Feb. 1, 2001—date provided by Google Search (see p. 3 of 4) (total pages 4) (Year: 2001).*
Kim et al., "A Study for the Removal of Phosphorous Using Coated Exfoliated Vermiculite," Journal of the Korean Geo-Environmental Society, 15 (12): 5-13, Dec. 2014 (Year: 2014).*
Ye, R. et al., "Preparation, Mechanical and Thermal Properties of Cement Board with Expanded Perlite Based Composite Phase Change Material for Improving Buildings Thermal Behavior", Materials, Nov. 13, 2015, vol. 8 (11), pp. 7702-7713.
Gerba, C. P., "Quaternary Ammonium Biocides: Efficacy in Application", Applied and Environmental Microbiology, Jan. 2015, vol. 81(2), pp. 464-469.
International Search Report and Written Opinion of the International Searching Authority of International Application No. PCT/US17/50337 dated Dec. 4, 2017.

* cited by examiner

*Primary Examiner* — Aradhana Sasan
(74) *Attorney, Agent, or Firm* — Ping Wang; Morris, Manning & Martin, LLP

(57) ABSTRACT

A method for formulating a cleaning composition contains the step of coating a granular absorbent material with a coating agent to produce a coated absorbent material and mixing the coated absorbent material with a sanitation agent, wherein the coated absorbent material absorbs the sanitation agent to form the cleaning composition. The resulting cleaning composition may be used for cleaning up pathogens or hazardous materials. The cleaning composition may also function as a liquefiable dry cleaning powder for public areas in response to bodily fluid incidents. A coating method of a non-toxic bio static film on a high surface area solid is disclosed.

7 Claims, No Drawings

CLEANING COMPOSITION, METHOD OF MAKING AND USE THEREOF

This application claims priority of U.S. Provisional Application Ser. No. 62/495,274, filed on Sep. 8, 2016. The entirety of which is incorporated herein by reference.

FIELD

The present application generally relates to a cleaning compositions and methods and, in particular, relates to a cleaning composition and method for cleaning up a surface, such as disinfecting, or removing a biohazard material from, a public area.

BACKGROUND

Typically, different types of disinfectants have been utilized as replacements to heat sterilization, radiation sterilization, or other less desirable techniques, in a variety of industries, including the pharmaceutical and medical industries, for some time. Disinfectants effectuate a safer, more cost effective and/or convenient means of eliminating potentially harmful germs, viruses, funguses and bacteria. However, the inherent strength of the chemical disinfectant has at times resulted in effectiveness and cost outweighing safety. Consequently, great care must be taken by the user regarding the nature of the use to which a chemical disinfectant is being put and there are stringent guidelines placed on all chemical disinfectant compositions.

SUMMARY

One aspect of the present application is directed to a method of formulating a cleaning composition, comprising the steps of: coating a granular absorbent material with a coating agent to produce a coated absorbent material; and mixing the coated absorbent material with a sanitation agent, wherein the coated absorbent material absorbs the sanitation agent to form the cleaning composition.

Another aspect of the present application directs to a cleaning composition, comprising an granular absorbent material coated with a biocide; and a sanitation agent absorbed in said granular absorbent material.

Another aspect of the present application directs to a method for prevention and/or decontamination of a surface from a pathogen, comprising: applying an effective amount of a cleaning composition on said surface, wherein said cleaning composition comprises an granular absorbent material coated with a biocide; and a sanitation agent absorbed in the granular absorbent material. In one embodiment, the pathogen is a virus or bacteria.

Yet, another aspect of the present application directs to a sanitation method, comprising the step of: applying an effective amount of the cleaning composition which comprises an granular absorbent material coated with a biocide; and a sanitation agent absorbed in said granular absorbent material to a surface in need of sanitation; and removing the cleaning composition after a period of time.

Another aspect of the present application directs to as a cleaning kit comprising the cleaning composition which comprises an granular absorbent material coated with a biocide; and a sanitation agent absorbed in said granular absorbent material to a surface in need of sanitation, and instructions on how to use the cleaning composition.

Another aspect of the application is a specialized coating method of a non-toxic bio static film on a high surface area solid, such as a granular absorbent material.

These and other aspects and embodiments of the present application will become better understood with reference to the following detailed description when considered in association with the accompanying drawings and claims.

DETAILED DESCRIPTION

The aspects of the application are described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it is understood that the particular value forms another embodiment. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

This application describes a novel, effective and low cost cleaning composition that can be used for rapid and safe clean-up of a surface. bio hazard spills (vomit/urine/blood and feces) in hospitals, urgent care facilities, medical offices, nursing homes, prisons, schools and the hospitality industry. This method and formulation is also ideally suited for common, highly hazardous spills in these environments, e.g., spills of chemotherapy drugs.

Method of Making

One aspect of the present application is directed to a method of making a cleaning composition. The method comprises the steps of coating a granular absorbent material with a coating agent to produce a coated absorbent material; and mixing the coated absorbent material with a sanitation agent, wherein the coated absorbent material absorbs the sanitation agent to form a coated and absorbed absorbent material. In some embodiments, the method further comprises the step of grinding an absorbent material to produce the granular absorbent material used in the coating step. In other embodiments, the method further comprises the step of adding one or more modifying agent to the coated and absorbed absorbent material in amounts sufficient to achieve desired physical characteristics (e.g., non-dusty and clump, ease of pick up, liquid loading capacity, etc.).

The cleaning composition may be used to eradicate, eliminate, inactivate, inhibit the activity of, or reduce the amount of pathogens on a surface. The cleaning composition is especially for the clean-up of biohazard spills, such as vomit, urine, blood and feces in hospitals, urgent care facilities, medical offices, nursing homes, prisons, schools and the hospitality industry. The cleaning composition of the present application is also ideally suited for clean-up of common, highly hazardous spills in these environments, such as spills of chemotherapy drugs.

The Granular Absorbent Material

The granular absorbent material can be any solid material with desired surface area, granulation, and absorbent characteristics. As used herein, the term "absorbent" or "adsorbent" is understood to mean a material that is capable of imbibing and holding onto aqueous fluids. Suitable granular absorbent material include, but are not limited to, expanded and optimized ceramic minerals such perlite and vermiculite, zeolite, activated carbon, cellulosic absorbents and fibrous absorbents. In some embodiments, the granular absorbent material contains activated carbon, fumed silica, fine perlite, zeolites, processed clays or combinations thereof. The adsorbent/absorbent will exhibit clumping or matting characteristics for best performance and be well de-dusted. The granular absorbent material preferably has a surface area per mass or volume ratio. In some embodiments, the granular absorbent material has a surface area per mass ratio in the range of 100-10,000 $m^2/g$, 100-9,000 $m^2/g$, 100-8,000 $m^2/g$, 300-8,000 $m^2/g$, 1,000-8,000 $m^2/g$, 2,000-8,000 $m^2/g$, 3,000-8,000 $m^2/g$, 4,000-8,000 $m^2/g$, 5,000-8,000 $m^2/g$, 6,000-8,000 $m^2/g$, 7,000-8,000 $m^2/g$, 100-7,000 $m^2/g$, 300-7,000 $m^2/g$, 1,000-7,000 $m^2/g$, 2,000-7,000 $m^2/g$, 3,000-7,000 $m^2/g$, 4,000-7,000 $m^2/g$, 5,000-7,000 $m^2/g$, 6,000-7,000 $m^2/g$, 100-6,000 $m^2/g$, 300-6,000 $m^2/g$, 1,000-6,000 $m^2/g$, 2,000-6,000 $m^2/g$, 3,000-6,000 $m^2/g$, 4,000-6,000 $m^2/g$, 5,000-6,000 $m^2/g$, 100-4,000 $m^2/g$, 300-4,000 $m^2/g$, 1,000-4,000 $m^2/g$, 2,000-4,000 $m^2/g$, 3,000-4,000 $m^2/g$, 100-3,000 $m^2/g$, 300-3,000 $m^2/g$, 1,000-3,000 $m^2/g$, 2,000-3,000 $m^2/g$, 100-2,000 $m^2/g$, 300-2,000 $m^2/g$, or 1,000-2,000 $m^2/g$.

In some embodiments, the granular absorbent material has a surface area per mass ratio up to 10,000 $m^2/g$. In some embodiments, the granular absorbent material has a surface area per mass ratio up to 9,000 $m^2/g$. In some embodiments, the granular absorbent material has a surface area per mass ratio up to 8,000 $m^2/g$. In some embodiments, the granular absorbent material has a surface area per mass ratio up to 7,000 $m^2/g$. In some embodiments, the granular absorbent material has a surface area per mass ratio up to 6,000 $m^2/g$.

In some embodiments, the granular absorbent material has a surface area per mass ratio of 100 $m^2/g$ or greater. In some embodiments, the granular absorbent material has a surface area per mass ratio of 300 $m^2/g$ or greater. In some embodiments, the granular absorbent material has a surface area per mass ratio of 1,000 $m^2/g$ or greater. In some embodiments, the granular absorbent material has a surface area per mass ratio of 2,000 $m^2/g$ or greater. In some embodiments, the granular absorbent material has a surface area per mass ratio of 3,000 $m^2/g$ or greater. In some embodiments, the granular absorbent material has a surface area per mass ratio of 4,000 $m^2/g$ or greater. In some embodiments, the granular absorbent material has a surface area per mass ratio of 5,000 $m^2/g$ or greater.

In some embodiments, the granular absorbent material has a surface area per mass ratio in the range of 1000-6,000 $m^2/g$.

In some embodiments, the granular absorbent material contains ceramic minerals.

In some embodiments, the granular absorbent material contains perlite and/or vermiculite.

In some embodiments, the granular absorbent material has a surface area per volume ratio in the range of 100-5,000 $m^2/ml$, 300-5,000 $m^2/ml$, 1,000-5,000 $m^2/ml$, 2,000-5,000 $m^2/ml$, 3,000-5,000 $m^2/ml$, 4,000-5,000 $m^2/ml$, 100-4,000 $m^2/ml$, 300-4,000 $m^2/ml$, 1,000-4,000 $m^2/ml$, 2,000-54,000 $m^2/ml$, 3,000-4,000 $m^2/ml$, 100-3,000 $m^2/ml$, 300-3,000 $m^2/ml$, 1,000-3,000 $m^2/ml$, 2,000-3,000 $m^2/ml$, 100-2,000 $m^2/ml$, 300-2,000 $m^2/ml$, or 1,000-2,000 $m^2/ml$.

In some embodiments, the granular absorbent material has a surface area per volume ratio up to 5,000 $m^2/ml$. In some embodiments, the granular absorbent material has a surface area per volume ratio up to 4,000 $m^2/ml$. In some embodiments, the granular absorbent material has a surface area per volume ratio up to 3,000 $m^2/ml$.

In some embodiments, the granular absorbent material has a surface area per volume ratio of 100 $m^2/ml$ or greater. In some embodiments, the granular absorbent material has a surface area per volume ratio of 300 $m^2/ml$ or greater. In some embodiments, the granular absorbent material has a surface area per volume ratio of 1,000 $m^2/ml$ or greater. In some embodiments, the granular absorbent material has a surface area per volume ratio of 2,000 $m^2/ml$ or greater. In some embodiments, the granular absorbent material has a surface area per volume ratio in the range of 1000-3,000 $m^2/ml$.

As used herein, the term "ceramics" shall mean compounds of nonmetallic elements possessing in general hardness, compressive strength, elastic modulus, thermal expansion and density. Exemplary ceramics include, but are not limited to, materials used in pottery, bricks, tiles, cements and glass, barium titanate, strontium titanate, bismuth strontium calcium copper oxide, boron oxide, boron nitride, earthenware, ferrite, lead zirconate titanate, magnesium diboride, porcelain, sialon, silicon carbodie, silicon nitride, steatite, titanium carbide, uranium oxide, yttrium barium copper oxide, zinc oxide, zirconium dioxide, and partially stabilized zirconia. Ceramics may be oxides (aluminia, beryllia, ceria, zirconia), nonoxides (carbide, boride, nitride, silicide) or composite materials (combinations of oxides and onoxides).

Perlite is a naturally occurring form of obsidian characterized by spherulites formed by cracking of volcanic glass during cooling. Perlite typically comprises a mix of silicon dioxide, aluminium oxide, sodium oxide, potassium oxide, iron oxide, magnesium oxide and calcium oxide. Potential substitutes for perlite include, but are not limited to, diatomite, expanded clay, shale, pumice, slag or vermiculite. Vermiculite is a naturally occurring hydrous phyllosilicate material, which is 2:1 clay.

As used herein, the term "zeolite" shall mean any of a large group of minerals comprising hydrated aluminosilicates of sodium, potassium, calcium and barium. Zeolite can occur naturally, but is also artificially synthesized. Exemplary zeolites include, but are not limited to, analcime, chabazite, clinoptilolite, heulandite, natrolite, phillipsite, and stilbite.

As used herein, the term "activated carbon" shall mean a form of carbon processed to have small, low-volume pores that increase the surface area available for adsorption or chemical reactions. A synonym for activate carbon is "activated charcoal."

As used herein, the term "cellulosic absorbents" shall mean cellulose and cellulose derivatives that can provide structure, bulk, water-holding capacity and channeling of fluids over a wide dimensional range.

As used herein, the term "fibrous absorbents" refers to a fibrous structure with high void volume, a hydrophilic nature, and wet resiliency. Examples of fibrous absorbents include, but are not limited to, cotton fiber based absorbents, corn fiber based absorbents and hemp based absorbents.

In some embodiments, the granular absorbent material constitutes 10-70% (w/w), 10-60% (w/w), 10-50% (w/w), 10-40% (w/w), 10-30% (w/w), 10-20% (w/w), 20-70% (w/w), 20-60% (w/w), 20-50% (w/w), 20-40% (w/w), 20-30% (w/w), 30-70% (w/w), 30-60% (w/w), 30-50% (w/w), 30-40% (w/w), 40-70% (w/w), 40-60% (w/w), 40-50% (w/w), 50-70% (w/w), 50-70% (w/w) or 60-70% (w/w) of the final product. In some embodiments, the granular absorbent material constitutes 25-30% (w/w) of the final product. In some embodiments, the granular absorbent material constitutes about 27% (w/w) of the final product.

The Coating Agent

The coating agent can be any biocide capable of forming a coating layer on the surface of the granular absorbent material of the present application. In some embodiments, the coating agent contains one or more agents selected from the group consisting of silanes, siloxanes, aminopropyltrimethoxysilane, quaternary amines, fumed metal hydroxides, solutions of silver, solutions of copper and combinations thereof.

In some embodiments, the coating agent is a biocide that forms a surface bonded film on the granular absorbent material. The static surface bonded biocide film provides a long term inactivation or inhibition of pathogens in contact with the cleaning composition of the present invention, thus providing a long term assurance of the effectiveness of the cleaning effect. In some embodiments, the coating agent is applied to the granular absorbent material by vapor deposition. In some embodiments, the vapor deposition is performed by thermal heating the coating agent and the granular absorbent.

In some embodiments, the coating agent is applied to the granular absorbent material by pressure micro droplet spray.

In some embodiments, the coating agent is applied to the granular absorbent material by a fuming or fogging nozzle.

In some embodiments, the coating agent is applied to the granular absorbent material by a deposition technique commonly used for metal plating.

As used herein, the term "biocide" refers to any material that destroys, inactivates, eliminates, deters, inhibits the growth of, or otherwise render harmless and/or prevent damage or infection of a pathogen or a microorganism. Examples of biocide includes, but are not limited to, silanes, siloxanes, aminopropyltrimethoxysilane, quaternary amines, fumed metal hydroxides, silver and salts or solutions thereof, copper and salts or solutions thereof, formaldehyde; bronopol; chlorocresol; peracetic acid; chloroxylenol; biphenyl-2-ol; hexa-2,4-dienoic acid/scorbutic acid; glutaral; clorofen; 2-phenoxyethanol; cetylpyridinium chloride; tosylchloramide sodium; sodium 2-biphenylate; phthalaldehyde; N-(3-aminopropyl)-N-dodecylpropan-1,3-diamine; troclosen sodium; sodium dichloroisocyanurate dihydrate; didecyldimethylammonium chloride; iodine; sodium hypochlorite; hydrogen peroxide; calcium hypochlorite; silver chloride; lignin; 2,2-dibromo-2-cyanoacetamide; sodium p-chloro-m-cresolate; d-gluconic acid compound with N,N"-bis(4-chlorophenyl)-3,12-diimino-2,4,11,13-tetraazatetradecanediamidine (2:1); potassium (E,E)-hexa-2,4-dienoate; quaternary ammonium compounds, benzyl-C12-18-alkyldimethyl-chlorides; benzyl-C12-16-alkyldimethyl-chlorides; di-C8-10-alkyldimethyl-chlorides; pentapotassium bis(peroxymonosulfate)-bis(sulfate); benzyl-C12-14-alkyldimethyl-chlorides; C12-14-alkyl[(ethylphenyl)methyl]dimethyl-chlorides; [2-[[2-[(2-carboxyethyl)(2-hydroxyethyl)-amino]ethyl]amino]-2-oxoethyl]-coco alkyldimethyl-hydroxides, internal salts; reaction products from: glutamic acid and N—(C12-14-alkyl)-propylenediamine; 6-(phthalimido)peroxyhexanoic acid; silver sodium hydrogen zirconium phosphate; poly (hexamethylendiamineguanidinium chloride); polyhexamethylene biguanide; oligo(2-(2-ethoxy)ethoxyethylguanidinium chloride) polymer; amines, n-C10-16-alkyltrimethylene di-, reaction products from chloroacetic acid; quaternary ammonium iodides; benzylalkyldimethyl (alkyl from C8-C22, saturated and unsaturated, and tallow alkyl, coco alkyl and soya alkyl), chlorides, bromides or hydroxides)/BKC; dialkyldimethyl(alkyl from C6-C18, saturated and unsaturated, and tallow alkyl, coco alkyl and soya alkyl) chlorides, bromides or methylsulfates)/DDAC; 2-butanone, peroxide; boric acid; disodium octaborate tetrahydrate; triclosan; melaleuca alternifolia, extract/Australian tea tree oil; sulfur dioxide; sodium hydrogen sulfite; disodium disulfite; sodium sulfite; potassium sulfite; dipotassium disulfite; 1-[[2-(2,4-di-chlorophenyl)-4-propyl-1,3-dioxolan-2-yl]methyl]-1H-1,2,4-triazol/propiconazole; triclocarban; dodecylguanidine monohydrochloride; silver zinc aluminum borophosphate glass/glass oxide, silver and zinc-containing; aluminum sodium silicate silver zinc complex/silver-zinc zeolite plant protection agents; sodium benzoate; disodium-tetraborate, anhydrous; mixture of cis and trans p-menthan-3,8-diol/citriodiol; mecetronium ethyl sulfate; amines, C10-16-alkyldimethyl-, N-oxides; calcium dihexa-2,4-dienoate; sodium hydrogen carbonate; benzoxonium chloride; benzethonium chloride; tetradonium bromide; polyvinylpyrrolidone-iodine; silver nitrate; N,N'-(decan-1,10-diyldi-1(4H)-pyridyl-4-yliden)bis (octylammonium)dichloride; 2,4,8,10-tetra(tert-butyl)-6-hydroxy-12H-dibenzo[d,g][1,3,2]dioxaphosphocin-6-oxide, sodium-salt.

As used herein, the term "silanes" refers chemical compounds with four substituents on silicon, including an organosilicon compound. Exemplary silanes include, but are not limited to, trichlorosilane ($SiHCl_3$), tetramethylsilane ($Si(CH_3)_4$) and tetraethoxysilane ($Si(OC_2H_5)_4$).

As used herein, the term "siloxanes" refers to chemical compounds that contain a functional group in organosilicon chemistry with the Si—O-Ai linkage. Exemplary siloxanes include, but are not limited to, polydimethylsiloxane or cyclomethicones.

As used herein, the term "pathogen" includes, but is not limited to, viruses, bacteria, yeast, protozoan, or other pathogenic microorganisms. Definitions and description of pathogens that may be eliminated, killed, inactivated or inhibited by administering the cleaning composition of the present application are described below. One of ordinary skill will understand that the described pathogens herein are not limiting. In some embodiments, the biocide and/or the cleaning composition of the present application can address such critical pathogen families as norovirus, HIV, MRSA, C. Diff., hepatitis, ebola, GI-related viruses of many sorts or targeted bioterror agents, amongst others defined and described below.

Examples of viruses include, but are not limited to, influenza viruses, herpesviruses, polioviruses, noroviruses, gastrointestinal tract-related (GI-related) viruses and retroviruses. Examples of viruses include, but are not limited to, human immunodeficiency virus type 1 and type 2 (HIV-1 and HIV-2), human T-cell lymphotropic virus type I and type II (HTLV-I and HTLV-II), hepatitis A virus, hepatitis B virus (HBV), hepatitis C virus (HCV), hepatitis delta virus (HDV), hepatitis E virus (HEV), hepatitis G virus (HGV), parvovirus B19 virus, transfusion transmitted virus (TTV), Epstein-Barr virus, human cytomegalovirus type 1 (HCMV-1), human herpesvirus type 6 (HHV-6), human herpesvirus type 7 (HHV-7), human herpesvirus type 8 (HHV-8), influenza type A viruses, including subtypes H1N1 and H5N1, influenza type B viruses, human metapneumovirus, severe acute respiratory syndrome (SARS) coronavirus, hantavirus, and RNA viruses from Arenaviridae (e.g., Lassa fever virus (LFV)), Pneumoviridae (e.g., human metapneumovirus), Filoviridae (e.g., Ebola virus (EBOV), Marburg virus (MBGV) and Zika virus); Bunyaviridae (e.g., Rift Valley fever virus (RVFV), Crimean-Congo hemorrhagic fever virus (CCHFV), and hantavirus); Flaviviridae (West Nile virus (WNV), Dengue fever virus (DENV), yellow fever virus (YFV), GB virus C (GBV-C; formerly known as hepatitis G virus (HGV)); Rotaviridae (e.g., rotavirus), human T-cell lymphotropic virus (HTLV) type I and type II (HTLV-I and HTLV-II), parvovirus B19 virus, transfusion transmitted virus (TTV); measles virus; rotaviruses, including Types A, B, C, D, and E; human papilloma virus (HPV) and its many serotypes; and other miscellaneous RNA viruses.

Examples of microbes caused causing gastroenteritis in man and animals include, viruses, bacteria, parasites and fungus. Viruses cause ~7-% of infectious diarrhea. Viral infections causing gastroenteritis can be attributed to rotavirus, adenovirus, norovirus, astrovirus, and coronavirus. Bacterial infections leading to gastroenteritis can be caused by *Campylobacter, Escherichia coli, Salmonella, Shigella, Staphylococcus aureus*, and *Clostridum* bacterial species. Protozoa infections leading to gastroenteritis can be a result of *Giardia, Entamoeba*, and *Cryptosporidium* species.

As used herein, the term "bacteria" shall mean members of a large group of unicellular microorganisms that have cell walls but lack organelles and an organized nucleus. Synonyms for bacteria include the terms "microorganisms", "microbes", "germs", "bacilli", "pathogens", and "prokaryotes." Exemplary bacteria include, but are not limited to *Mycobacterium* species, including *M. tuberculosis; Staphylococcus* species, including *S. epidermidis, S. aureus*, and methicillin-resistant *S. aureus; Streptococcus* species, including *S. pneumoniae, S. pyogenes, S. mutans, S. agalactiae, S. equi, S. canis, S. bovis, S. equinus, S. anginosus, S. sanguis, S. salivarius, S. mitis*; other pathogenic Streptococcal species, including *Enterococcus* species, such as *E. faecalis* and *E. faecium; Haemophilus influenzae, Pseudomonas* species, including *P. aeruginosa, P. pseudomallei*, and *P. mallei; Salmonella* species, including *S. enterocolitis, S. typhimurium, S. enteritidis, S. bongori*, and *S. choleraesuis; Shigella* species, including *S. flexneri, S. sonnei, S. dysenteriae*, and *S. boydii; Brucella* species, including *B. melitensis, B. suis, B. abortus*, and *B. pertussis; Neisseria* species, including *N. meningitidis* and *N. gonorrhoeae; Escherichia coli*, including enterotoxigenic *E. coli* (ETEC); *Vibrio cholerae, Helicobacter pylori, Chlamydia trachomatis, Clostridium difficile, Cryptococcus neoformans, Moraxella* species, including *M. catarrhalis, Campylobacter* species, including *C. jejuni; Corynebacterium* species, including *C. diphtheriae, C. ulcerans, C. pseudotuberculosis, C. pseudodiphtheriticum, C. urealyticum, C. hemolyticum, C. equi; Listeria monocytogenes, Nocardia asteroides, Bacteroides* species, *Actinomycetes* species, *Treponema pallidum, Leptospirosa* species, *Klebsiella pneumoniae; Proteus* sp., including *Proteus vulgaris; Serratia* species, *Acinetobacter, Yersinia* species, including *Y. pestis* and *Y. pseudotuberculosis; Francisella tularensis, Enterobacter* species, *Bacteroides* species, *Legionella* species, *Borrelia burgdorferi*, and the like.

As used herein, the term "MRSA" shall mean the gram-positive bacterium methicillin-resistant *Staphylococcus aureus* (MRSA). The term MRSA encompasses any strain of *S. aureus* that has developed, through horizontal gene transfer and natural selection, multiple drug resistance to beta-lactam antibiotics.

As used herein, the term "*C. Diff.*" shall mean a species of gram-positive spore-forming bacterium known as *Clostridium difficile*, or *C. difficile*, or *C. diff* or sometimes CDF/cdf. *Clostridium difficile* infection (CDI) is a symptomatic infection caused by this bacteria which can cause *C. difficile* associated diarrhea or *Clostridum difficile* colitis.

As used herein, the term "fungi" shall mean any member of the group of saprophytic and parasitic spore-producing eukaryotic typically filamentous organisms formerly classified as plants that lack chlorophyll and include molds, rusts, mildews, smuts, mushrooms, and yeasts. Exemplary fungi include, but are not limited to, *Aspergillus* species, *Dermatophytes, Blastomyces derinatitidis, Candida* species, including *C. albicans* and *C. krusei; Malassezia furfur, Exophiala werneckii, Piedraia hortai, Trichosporon beigelii, Pseudallescheria boydii, Pneumocystis jiroveci, Madurella grisea, Histoplasma capsulatum, Sporothrix schenckii, Histoplasma capsulatum, Tinea* species, including *T. versicolor, T. pedis T. unguium, T. cruris, T. capitus, T. corporis, T. barbae; Trichophyton* species, including *T. rubrum, T. interdigitale, T. tonsurans, T. violaceum, T. yaoundei, T. schoenleinii, T. megninii, T. soudanense, T. equinum, T. erinacei*, and *T. verrucosum; Mycoplasma genitalia; Microsporum* species, including *M. audouini, M. ferrugineum, M. canis, M. nanum, M. distortum, M. gypseum, M. fulvum*, and the like.

As used herein, the term "protozoan" shall mean any member of a diverse group of eukaryotes that are primarily unicellular, existing singly or aggregating into colonies, are usually nonphotosynthetic, and are often classified further into phyla according to their capacity for and means of motility, as by pseudopods, flagella, or cilia. Exemplary protozoans include, but are not limited to *Plasmodium* species, including *P. falciparum, P. vivax, P. ovale*, and *P. malariae; Leishmania* species, including *L. major, L. tropica, L. donovani, L. infantum, L. chagasi, L. mexicana, L. panamensis, L. braziliensis* and *L. guyanensi; Cryptosporidium, Isospora belli, Toxoplasma gondii, Trichomonas vaginalis*, and *Cyclospora* species.

As used herein, the term "targeted bioterror agents" includes, but is not limited to, anthrax (*Bacillus anthracis*), botulism (*Clostridium botulinum* toxin), plague (*Yersinia pestis*), smallpox (Variola virus), tularemia (*Franciscella tularensis*) and viral hemorrhagic fever (arenaviruses, bunyaviruses, filoviruses, and arenaviruses), or other CDC Category A Agents. *Brucella* species, *Clostrodium perfringens, Salmonella* species, *Escherichia coli*, and *Shigella* species, *Burkholderia mallei, Burkholderia pseudomallei, Chlamydia psittaci, Coxiella brunetii, Ricinus communis, Rickettsia prowazekii, Vibrio cholera*, and *Cryptosporidium parvum*, and alphaviruses, e.g., Venezuelan equine encephalitis, eastern equine encephalitis, and western equine encephalitis viruses and other CDC Category B Agents. Emerging infectious disease infectious agents such as Nipah virus, hantavirus and other CDC Category C Agents.

In some embodiments, the coating agent is added in an amount that constitutes 0.1 to 10% (w/w), 0.1 to 5% (w/w), 0.1 to 2% (w/w), 0.1 to 1% (w/w), 0.1 to 0.5% (w/w), 0.3 to 10% (w/w), 0.3 to 5% (w/w), 0.3 to 2% (w/w), 0.3 to 1% (w/w), 1 to 10% (w/w), 1 to 5% (w/w), 1 to 2% (w/w), 3 to 10% (w/w) or 3 to 5% (w/w) of the final product.

In some embodiments, the coating agent is added in an amount that constitutes 0.5 to 3.5% (w/w) or 1 to 3% (w/w) of the final product. In some embodiments, the coating agent is added in an amount that constitutes about 2% (w/w) of the final product.

The Sanitation Agent

The sanitation agent can be any agent having biocide activity and can be absorbed by the coated granular absorbent of the present application. The sanitation agent comprise an active substance designed to destroy, inhibit, reduce activity, inhibit grow or otherwise render harmless harmful organisms or toxic chemicals. In some embodiments, the sanitation agent is a liquid phase agent. In some embodiment, the sanitation agent is a liquid phase biocide. In some embodiment, the sanitation agent is a liquid phase chemical that inactivates or removes toxic chemicals, such as chemo therapy drugs. In some embodiments, the liquid phase biocide is added at an application site to provide chemical disinfection for immediate response.

Examples of liquid phase biocide include, but are not limited to, chlorine bleach solutions, hydrogen peroxide solutions, peracetic acid, quaternary amine solutions, alcohol solutions, periodine solutions, dimethyl benzyl ammonium chloride, dimethyl ethybenzyl ammonium chloride and mixtures thereof.

Examples of liquid phase chemicals that can be used to inactivate or remove toxic chemicals include, but are not limited to, anionic surfactants such as soap, sulfonates and sulfates. In some embodiments, large quantities of water is used to dilute the toxic chemicals.

In some embodiments, the sanitation agent is added in an amount that constitutes 0.1 to 10% (w/w), 0.1 to 3% (w/w), 0.1 to 1% (w/w), 0.1 to 0.3% (w/w), 0.3 to 10% (w/w), 0.3 to 3% (w/w), 0.3 to 1% (w/w), 1 to 10% (w/w), 1 to 3% (w/w) or 3 to 10% (w/w) of the final product.

In some embodiments, the sanitation agent comprises dimethyl benzyl ammonium chloride or dimethyl ethybenzyl ammonium chloride. In some embodiments, the sanitation agent comprises a mixture of dimethyl benzyl ammonium chloride or dimethyl ethybenzyl ammonium chloride. In some embodiments, the sanitation agent is a 1:1 mixture of dimethyl benzyl ammonium chloride or dimethyl ethybenzyl ammonium chloride.

In some embodiments, the sanitation agent is a quatanary amine and is added in an amount that constitutes 0.3 to 3% (w/w), 0.5 to 2% (w/w) or 0.5 to 1.5% (w/w) of the final product. In some embodiments, the sanitation agent is a quatanary amine and is added in an amount that constitutes about 1% (w/w) of the final product.

The Modifying Agent

The modifying agent is added to the coated granular absorbent or the absorbed-and-coated granular absorbent in an amount to achieve desired physical characteristics (e.g., non-dusty and clump, ease of pick up, liquid loadability, etc.) in the final product. Examples of the modifying agent include, but are not limited to, thickening agents, gums, absorbent polymers, tackifiers, and combinations thereof.

As used herein, the term "thickening agent" may include any material known or otherwise effective in providing suspending, gelling, viscosifying, solidifying or thickening properties to the composition or which otherwise provide structure to the final product form. These thickening agents may include gelling agents, polymeric or nonpolymeric agents, inorganic thickening agents, or viscosifying agents. The amount and type of the thickening agent may vary depending upon the desired characteristics of the final product.

As used herein, the term "tackifier" refers to polymeric adhesives which increase the tack, i.e., the inherent stickiness or self-adhesion, of the compositions so that after a short period of gentle pressure they adhere firmly to surfaces. Examples of suitable tackifiers comprise high-flexibility resins such as, but not limited to, homopolymers of alkyl(meth)acrylates, especially alkyl acrylates, such as poly(isobutyl acrylate) or poly(2-ethylhexyl acrylate), linear polyesters, as commonly used for coil coating, linear difunctional oligomers, curable with actinic radiation, with a number average molecular weight of more than 2000, in particular from 3000 to 4000, based on polycarbonatediol or polyester-diol, linear vinyl ether homopolymers or copolymers based on ethyl, propyl, isobutyl, butyl and/or 2-ethylhexyl vinyl ether, or nonreactive urethane urea oligomers, which are prepared from bis(4,4-isocyanatophenyl)methane, N,N-dimethylethanolamine or diols such as propanediol, hexanediol or dimethylpentanediol.

In some embodiments, the modifying agent comprises a high-molecular substance that absorbs liquids, preferably water, swells, and finally is converted to a viscous true or colloidal solution.

In some embodiments, the modifying agent comprises one or more silicone gums. As used herein, the term "silicone gum" means a silicone polymer having a degree of polymerization sufficient to provide a silicone having a gum-like texture. In certain cases the silicone polymer forming the gum may be crosslinked.

In some embodiments, the modifying agent comprises a polymer. As used herein, Examples of the polymers include, but is not limited to, natural and synthetic polymers such as polyacrylamide (ACAM) and carboxymethyl cellulose.

In some embodiments, the polymers of the present application includes, but are not limited to, polyacrylates such as sodium polyacrylates, and carboxymethyl cellulose.

In some embodiments, the modifying agent comprises one or more super-absorbent polymer. The term "super-absorbent polymer" is understood to mean hydrophilic polymer structure capable of absorbing water or saline solution at greater than 10 g of pure water/saline per gram of dry-based material (>10 g/g). Examples of super-absorbent polymers include, but are not limited to, sodium polyacrylates and carboxymethyl cellulose.

In some embodiments, the one or more modifying agents further comprise one or more additives selected from the group comprising denaturing agents, colorant agents, odor correctors, and/or pH regulators.

In some embodiments, the one or more modifying agents are added in an amount that constitute 0.1 to 5% (w/w), 0.1 to 2% (w/w), 0.1 to 1% (w/w), 0.1 to 0.3% (w/w), 0.3 to 5% (w/w), 0.3 to 2% (w/w), 0.3 to 1% (w/w), 1 to 5% (w/w), 1 to 2% (w/w) or 2 to 5% (w/w) of the final product.

The Cleaning Composition

Another aspect of the present application relates to a cleaning composition. The cleaning composition contains an granular absorbent material coated with a coating agent. Examples of the coating agent have been described above.

In some embodiments, the coating agent contains a biocide. In some embodiments, the biocide comprises an agent selected from the group consisting of silanes, siloxanes, aminopropyltrimethoxysilane, quaternary amines, fumed metal hydroxides, silver and salts of silver, copper and salts of copper. In some embodiments, the biocide forms a static film on the surface of the granular absorbent material. In some embodiments, the granular absorbent material contains activated carbon, fumed silica, fine perlite, zeolites, processed clays or combinations thereof. In some embodiments, the coating agent constitutes 0.1 to 5% (w/w), 0.1 to 2% (w/w), 0.1 to 1% (w/w), 0.1 to 0.3% (w/w), 0.3 to 5% (w/w), 0.3 to 2% (w/w), 0.3 to 1% (w/w), 1 to 5% (w/w), 1 to 2% (w/w) or 2 to 5% (w/w) of the cleaning composition.

In some embodiments, the granular absorbent material contains ceramic minerals. In some embodiments, the granular absorbent material contains perlite and/or vermiculite. In some embodiments, the granular absorbent material has a surface area per mass ratio in the range of 100-10,000 $m^2/g$, 100-9,000 $m^2/g$, 100-8,000 $m^2/g$, 300-8,000 $m^2/g$, 1,000-8,000 $m^2/g$, 2,000-8,000 $m^2/g$, 3,000-8,000 $m^2/g$, 4,000-8,000 $m^2/g$, 5,000-8,000 $m^2/g$, 6,000-8,000 $m^2/g$, 7,000-8,000 $m^2/g$, 100-7,000 $m^2/g$, 300-7,000 $m^2/g$, 1,000-7,000 $m^2/g$, 2,000-7,000 $m^2/g$, 3,000-7,000 $m^2/g$, 4,000-7,000 $m^2/g$, 5,000-7,000 $m^2/g$, 6,000-7,000 $m^2/g$, 100-6,000 $m^2/g$, 300-6,000 $m^2/g$, 1,000-6,000 $m^2/g$, 2,000-6,000 $m^2/g$, 3,000-6,000 $m^2/g$, 4,000-6,000 $m^2/g$, 5,000-6,000 $m^2/g$, 100-4,000 $m^2/g$, 300-4,000 $m^2/g$, 1,000-4,000 $m^2/g$, 2,000-4,000 $m^2/g$, 3,000-4,000 $m^2/g$, 100-3,000 $m^2/g$, 300-3,000 $m^2/g$, 1,000-3,000 $m^2/g$, 2,000-3,000 $m^2/g$, 100-2,000 $m^2/g$, 300-2,000 $m^2/g$, or 1,000-2,000 $m^2/g$.

In some embodiments, the granular absorbent material has a surface area per mass ratio up to 10,000 $m^2/g$. In some embodiments, the granular absorbent material has a surface area per mass ratio up to 9,000 $m^2/g$. In some embodiments, the granular absorbent material has a surface area per mass ratio up to 8,000 $m^2/g$. In some embodiments, the granular absorbent material has a surface area per mass ratio up to 7,000 $m^2/g$. In some embodiments, the granular absorbent material has a surface area per mass ratio up to 6,000 $m^2/g$.

In some embodiments, the granular absorbent material has a surface area per mass ratio of 100 $m^2/g$ or greater. In some embodiments, the granular absorbent material has a surface area per mass ratio of 300 $m^2/g$ or greater. In some embodiments, the granular absorbent material has a surface area per mass ratio of 1,000 $m^2/g$ or greater. In some embodiments, the granular absorbent material has a surface area per mass ratio of 2,000 $m^2/g$ or greater. In some embodiments, the granular absorbent material has a surface area per mass ratio of 3,000 $m^2/g$ or greater. In some embodiments, the granular absorbent material has a surface area per mass ratio of 4,000 $m^2/g$ or greater. In some embodiments, the granular absorbent material has a surface area per mass ratio of 5,000 $m^2/g$ or greater.

In some embodiments, the granular absorbent material has a surface area per mass ratio in the range of 1000-6,000 $m^2/g$.

In some embodiments, the granular absorbent material has a surface area per volume ratio in the range of 100-5,000 $m^2/ml$, 300-5,000 $m^2/ml$, 1,000-5,000 $m^2/ml$, 2,000-5,000 $m^2/ml$, 3,000-5,000 $m^2/ml$, 4,000-5,000 $m^2/ml$, 100-4,000 $m^2/ml$, 300-4,000 $m^2/ml$, 1,000-4,000 $m^2/ml$, 2,000-54,000 $m^2/ml$, 3,000-4,000 $m^2/ml$, 100-3,000 $m^2/ml$, 300-3,000 $m^2/ml$, 1,000-3,000 $m^2/ml$, 2,000-3,000 $m^2/ml$, 100-2,000 $m^2/ml$, 300-2,000 $m^2/ml$, or 1,000-2,000 $m^2/ml$.

In some embodiments, the granular absorbent material has a surface area per volume ratio up to 5,000 $m^2/ml$. In some embodiments, the granular absorbent material has a surface area per volume ratio up to 4,000 $m^2/ml$. In some embodiments, the granular absorbent material has a surface area per volume ratio up to 3,000 $m^2/ml$.

In some embodiments, the granular absorbent material has a surface area per volume ratio of 100 $m^2/ml$ or greater. In some embodiments, the granular absorbent material has a surface area per volume ratio of 300 $m^2/ml$ or greater. In some embodiments, the granular absorbent material has a surface area per volume ratio of 1,000 $m^2/ml$ or greater. In some embodiments, the granular absorbent material has a surface area per volume ratio of 2,000 $m^2/ml$ or greater. In some embodiments, the granular absorbent material has a surface area per volume ratio in the range of 1000-3,000 $m^2/ml$.

In some embodiments, the granular absorbent material constitutes 10-70% (w/w), 10-60% (w/w), 10-50% (w/w), 10-40% (w/w), 10-30% (w/w), 10-20% (w/w), 20-70% (w/w), 20-60% (w/w), 20-50% (w/w), 20-40% (w/w), 20-30% (w/w), 30-70% (w/w), 30-60% (w/w), 30-50% (w/w), 30-40% (w/w), 40-70% (w/w), 40-60% (w/w), 40-50% (w/w), 50-70% (w/w), 50-70% (w/w) or 60-70% (w/w) of the cleaning composition. In some embodiments, the granular absorbent material constitutes 25-30% (w/w) of the final product. In some embodiments, the granular absorbent material constitutes about 27% (w/w) of the cleaning composition.

In some embodiments, the cleaning composition further comprises a sanitation agent absorbed in the coated granular absorbent material. Examples of the sanitation agent have been described above.

In some embodiments, the sanitation agent comprise an active substance designed to destroy, inhibit, reduce activity, inhibit grow or otherwise render harmless harmful organisms or toxic chemicals. In some embodiments, the sanitation agent is a liquid phase agent. In some embodiment, the sanitation agent is a liquid phase biocide. In some embodiment, the sanitation agent is a liquid phase chemical that inactivates toxic chemicals, such as chemo therapy drugs.

Examples of liquid phase biocide include, but are not limited to, chlorine bleach solutions, hydrogen peroxide solutions, peracetic acid, quaternary amine solutions, periodine, alcohol solutions, dimethyl benzyl ammonium chloride, dimethyl ethybenzyl ammonium chloride and mixtures thereof.

Examples of liquid phase chemicals that can be used to inactivate or remove toxic chemicals include, but are not limited to, anionic surfactants such as soap, sulfonates and sulfates. In some embodiments, large quantities of water is used to dilute the toxic chemicals.

In some embodiments, the sanitation agent constitutes 0.1 to 10% (w/w), 0.1 to 3% (w/w), 0.1 to 1% (w/w), 0.1 to 0.3% (w/w), 0.3 to 10% (w/w), 0.3 to 3% (w/w), 0.3 to 1% (w/w), 1 to 10% (w/w), 1 to 3% (w/w) or 3 to 10% (w/w) of the cleaning composition.

In some embodiments, the sanitation agent comprises dimethyl benzyl ammonium chloride or dimethyl ethybenzyl ammonium chloride. In some embodiments, the sanitation agent comprises a mixture of dimethyl benzyl ammonium chloride or dimethyl ethybenzyl ammonium chloride. In some embodiments, the sanitation agent is a 1:1 mixture of dimethyl benzyl ammonium chloride or dimethyl ethybenzyl ammonium chloride.

In some embodiments, the cleaning composition further comprises one or more modifying agent. Examples of the sanitation agent have been described above. In some embodiments, the modifying agent comprises a thickening agent, a tackifier, a gum, an absorbent polymers or combinations thereof. In some embodiments, the one or more modifying agents comprise a carboxymethyl cellulose (CMC)-derived polymer and/or a hierarchically porous carbons (HPC)-derived polymer.

In some embodiments, the one or more modifying agents further comprise one or more additives selected from the group comprising denaturing agents, colorant agents, odor correctors, and/or pH regulators.

In some embodiments, the one or more modifying agents constitute 0.1 to 5% (w/w), 0.1 to 2% (w/w), 0.1 to 1% (w/w), 0.1 to 0.3% (w/w), 0.3 to 5% (w/w), 0.3 to 2% (w/w), 0.3 to 1% (w/w), 1 to 5% (w/w), 1 to 2% (w/w) or 2 to 5% (w/w) of the cleaning composition.

In some embodiments, the cleaning composition has a liquid loading capability in the range of 10-50% by volume, 15-45% by volume, 20-40% by volume, 25-35% by volume, or 25-30% by volume. In other embodiments, the cleaning composition has a liquid loading capability of 100-400% by mass addition, 150-350% by mass addition, or 200-300% by mass addition. In some embodiments, the cleaning composition of the present application is capable of absorbing liquid at a liquid loading of 25-30% by volume or 200-300% by mass addition.

Method of Use

Another aspect of the present application relates to a method of using the cleaning composition of the present application. The method comprises the steps of applying an effective amount of the cleaning composition of the present application to a surface in need of cleaning, and remove the cleaning composition after a period of time.

In some embodiments, the period of time is from 30 seconds to 30 minutes. In some embodiments, the period of time is from 1 to 30 minutes, from 1 to 20 minutes, from 1 to 10 minutes, from 2 to 30 minutes, from 2 to 20 minutes, from 2 to 10 minutes, from 5 to 30 minutes, from 5 to 20 minutes and from 5 to 10 minutes.

In some embodiments, the surface in need of cleaning comprises a biohazard spill. In some embodiments, the biohazard spill is vomit, urine, blood, feces, and/or a chemo therapy drug. In some embodiments, the surface in need of cleaning is a surface in a public area and needs to be treated to prevent or reduce cross contamination or infection. As used herein, the term "public area" includes, but is not limited to, hospitals, doctors' offices, urgent care facilities, nursing homes, prisons and related correction facilities, schools, buses, aircraft, airports, bars, restaurants, hotels, amusement parks, any large gathering institution facilities, veterinary facilities and drug research and development facilities. In some embodiments, the public area is located in a hotel.

In some embodiments, the method further comprises the step of: washing the treated surface with a liquid or wiping the surface with a wiping material, such as paper tower or mops, after the removal of the cleaning composition.

Another aspect of the present application relates to a method of disinfecting an affected area to prevent or reduce the distribution of pathogens such as viruses and bacteria. The method comprises the steps of apply an effective amount of the cleaning composition of the present application to the affected area and remove the cleaning composition after a period of time, wherein the cleaning composition contains a granular absorbent material coated with a static, surface bonded film of biocide selected from the group consisting of silanes, siloxanes, aminopropyltrimethoxysilane, quaternary amines, fumed metal hydroxides, silver and salts of silver, copper and salts of copper. In some embodiments, the cleaning composition further comprises a sanitation agent selected from the group consisting of chlorine bleach solutions, hydrogen peroxide solutions, per acetic acid, quaternary amine solutions and alcohol solutions. In some embodiments, the sanitation agent is added to the cleaning composition immediately prior to the application to the affected area.

In some embodiments, the cleaning composition of the present application is a multi-phase product that can be used to kill microbes through a number of different mechanisms. In one embodiment, the composition is a doped granular ceramic disinfectant which combines a surface area static disinfectant or biocide coating with a chemical phase primary disinfectant or biocide absorbed in the ceramic particles. As used herein, the term "disinfectant" describes the composition and formulations described herein for the elimination of pathogens from surfaces. As used herein, the term "disinfect" shall mean the elimination of many or all pathogens on a surface to which disinfectant is administered.

In some embodiments, the cleaning composition of the present application is a surface area solid phase disinfectant that combines with a super absorbent polymer so that liquid loadings (e.g., 25-30% by volume/200-300% by mass addition) of available liquid can be added so as to impart chemical disinfection, to impart deodorizing chemicals or to impart a blanketing effect on the affected area so as to reduce the spread of microbe into the open air.

In some embodiments, the cleaning composition of the present application is a high surface area solid phase disinfectant with the addition of tackifiers, so that it lays on a bio hazard and forms a blanket which greatly reduces the release of airborne pathogens.

The following examples are offered by way of illustration of certain embodiments of aspects of the application herein. None of the examples should be considered limiting on the scope of the application.

Kits

Another aspect of the present application relates to a cleaning kit. The kit can be used for cleaning up hazardous materials, such as vomit, urine, blood, feces, and/or a spill of chemo therapy drug, or disinfecting a surface. In some embodiments, the kit contains the cleaning composition of the present application and instructions on how to use the cleaning composition.

In some embodiments, the kit further contains a copy of OSHA guidelines. In some embodiments, the kit further contains one or more of the following: biohazard bags, gloves, twist tie, antimicrobial hand wipe, germicidal wipe, scoop/scraper.

The cleaning kit can be conveniently placed in locations within quick reach of all caregivers. For example; all patient and chemotherapy rooms, case & crash carts, emergency vehicles, cafeteria, environmental services closets, and within or near first aid kits, etc.

Example 1: Tests of the Virucidal Effect of the Cleaning Composition of the Present Application Grow VR-728 Feline Calicivirus Strain F-9

Materials: CCL-94 cells, T-75 flask with CCL-94 cells, 70% confluent, 6 well plates with CCL-94 cells, 70% confluent, EMEM, FBS, VR-728 Feline calicivirus Strain F-9, 50 ml conical tube, Serological pipette, stripettes, 35° C. Incubator, CleanUp.

Methods

1. Viral stock=1:10 dilution, 1 ml virus+9 ml serum free EMEM

2. Remove medium from all flasks and plates
3. Add serum free media and virus to each flask and plat
   a. Flask 1: 2 ml virus+8 ml media
   b. Flask 2: 1.5 ml virus+8.5 ml media
   c. Plate 1: virus+media in all 6 cells
   d. Plate 2

| 13 mg clean up | 7.5 mg Clean Up | Virus |
| 1 mL media | 1 ml media | Media |
| | | Cells |
| 13 mg clean up | 7.5 mg Clean Up | Virus |
| 1 mL media | 1 ml media | Media |
| | | Cells |

4. Incubate at 35° C. for 1½ hours
5. Prepare media: EMEM+2% FBS and filter
6. Add 15 ml media to each flask
7. Add 1 ml media to each well in each plate Harvest VR-728 Feline Calicivirus Strain F-9
1. Combine media from Flask 1 and 2 and Plate 1
2. Cells were divided into 10, 15 ml conical tubes containing 10 ml virus each
3. Store at −80° C.

Materials: VR-728 Feline calicivirus Strain F-9, EMEM+ 2% FBS, CleanUp, 6-well plates with CCL-94 Cells, 70% confluent, Beaker, 1.5 ml centrifuge Tube, Centrifuge, 35° C. incubator, Cell Scraper, Cell Counter Methods
1. Virus diluted in EMEM+2% FBS at 1:50.
2. Measure 2 sets of 2 g, 3 g, 4 g, 5 g, 6 g of CleanUp and place each in a separate beaker. one set for 5 minutes, and one set for 10 minutes, autoclave.
3. Add 4 ml virus to 6 ml Cleaning Powder and allow it to sit for 5 minutes.
4. Remove Clean Up from each beaker.
5. Add 3 ml media to each beaker.
6. Repeat steps 3-5 for 10 minutes.
7. Take 1 ml from each beaker and add to a 1.5 ml centrifuge tube. Centrifuge at 2200 RPM, 4° C., 4 minutes.
8. Remove media from plate containing CCL-94 cells.
9. Add 30 µl Clean Up and 3 ml media to each well
10. Incubate for one hour.
11. Scrape Cells and place media into 15 ml tubes.
12. Determine cell death Plate Set-Up

| Cells + 1 g Clean Up | Cells + 1 g Clean Up | Cells |
| Cells + Virus | Cells + Virus | Cells |

Results

Compared to untreated virus samples, virus samples treated with CleanUp showed significantly reduced cytotoxicity, indicating activation of the virus by CleanUp.

Example 2: Tests of the Cleaning Composition of the Present Application with the Initial Virucidal Effectiveness Test The virucidal effect of the cleaning composition of the present application is further tested using the Initial Virucidal Effectiveness Test protocol provided by the Antimicrobials Division of the United States Environmental Protection Agency (USEPA).

Briefly, this test is designed to validate virucidal effectiveness claims for a product to be registered as a virucide. It determines the potential of the test agent to disinfect hard, non-porous surfaces contaminated with NOROVIRUS. This test is designed to simulate consumer use, conforms to EPA Guidelines DIS/TSS-7, November 1981, and follows the general procedure outlined in the FR notice for another surrogate virus available online1 and Virucidal Testing Format and Statistics Primer issued by EPA (March 2000).

Testing Conditions:

Two lots of the test agents will be used to inactivate the challenge virus that has been dried on a sterile glass surface (two replicates for each batch/lot of the test agents). The test agent will be tested in a manner consistent with the label directions for use of the test agent or as specified by the Sponsor.

Materials:

A. Test control and reference substances: supplied by the Sponsor (see last page)_The test agent will be tested as supplied by the Sponsor unless directed otherwise. The Sponsor, before the initiation of testing, must specify all operations performed on the test agent such as dilutions of the test agent, the diluent for the test agent, or specialized storage conditions.

The test agent must be tested for identity, strength, purity, stability and uniformity as applicable. All unused test agent will be retained for a period after completion of the test, then discarded in a manner that meets the approval of the safety officer.

B. Materials can include, but are not limited to:
1. Challenge virus as requested by the sponsor of the study: Feline calicivirus (American Type Culture Collection, Manassas, Va.; ATCC VR-782).
2. Host cell line: Crandel Reese Feline Kidney (CRFK) cell (American Type Culture Collection, Manassas, Va.; ATCC CCL-94).). CRFK cells will be grown in Cell Culture Media (Eagle's Minimum Essential Media containing $5% Fetal Bovine Serum) containing Fetal Bovine Serum (FBS). The FCV will be grown by inoculating confluent cell monolayers, no more than 24-48 hours in age, using low multiplicity of infection (MOI). Briefly, a flask of host cells grown in cell culture media containing 10% fetal bovine serum (FBS) will be used. The percent FBS contained in the stock virus aliquot will be adjusted to yield a minimum of a 5% organic soil load. Cells will be washed three times with phosphate buffered saline (PBS) and inoculated with virus. Post-virus adsorption, the cell monolayer will be washed once in Earle's balanced salt solution (EBSS), re-fed with cell culture media and incubated. The cytopathic effects (CPE) will be described as small, rounding of the cells, with a slight granular look. The CPE will start to develop in 1-2 days following inoculation, and will be harvested when more than 90% cytopathic effects (CPE) are observed. Post-incubation, the cells will be disrupted, with cell debris removed by centrifugation. Stock virus will be prepared by collecting the supernatant culture fluid from 75-100% infected culture cells. The supernatant will be removed, aliquoted, and stored in an ultra-low temperature freezer until the day of use. On the day of use an aliquot will be removed, thawed and refrigerated until use in the assay.
3. Laboratory equipment and supplies, and
4. Media and reagent:
   a. Cell Culture Media (Eagle's Minimum Essential Media containing $5% Fetal Bovine Serum)
   b. Earle's Balanced Salt Solution (EBSS)
   c. Fetal Bovine Serum (FBS)
   d. Phosphate Buffered Saline (PBS)

e. Sephadex™/Sephacryl™ columns (if necessary)
f. Neutralizer

Test System Identification:

All Petri dishes, dilution tube racks, and host-containing apparatus will be labeled with the following information: virus, host, test agent, and project number.

Experimental Design:

A. Inoculum preparation: The F-9 strain of Feline calicivirus (FCV) will be obtained from the American Type Culture Collection, Manassas, Va., (ATCC VR-782). The FCV will be grown by inoculating confluent cell monolayers, no more than 24-48 hours in age, using low multiplicity of infection (MOI). Briefly, a flask of host cells grown in cell culture media containing 10% fetal bovine serum (FBS) will be used. Cells will be washed three times with phosphate buffered saline (PBS) and inoculated with virus. Post-virus adsorption, the cell monolayer will be washed once in Earle's balanced salt solution (EBSS), re-fed with cell culture media and incubated. The cytopathic effects (CPE) are described as small, rounding of the cells, with a slight granular look. The CPE starts to develop in 1-2 days following inoculation, and will be harvested when more than ninety percent cytopathic effects (CPE) are observed. Post-incubation, the cells will be disrupted, with cell debris removed by centrifugation.

Stock virus will be prepared by collecting the supernatant culture fluid from 75-100% infected culture cells. The supernatant will be removed, aliquoted, and stored in an ultra-low temperature freezer until the day of use. On the day of use an aliquot is removed, thawed and refrigerated until use in the assay. The percent FBS contained in the stock virus aliquot is adjusted to yield a minimum of a 5% organic soil load. If the Sponsor chooses a soil load greater than 5%, the percent FBS contained in the stock virus aliquot will be adjusted to yield the percent soil load requested.

B. Carrier Preparation: An aliquot of 0.2 ml stock virus will be spread uniformly over the bottoms of 100×15 mm sterile glass Petri dishes with a cell scraper. The virus will be air-dried at room temperature for 30-60 minutes (until visibly dry). The drying conditions (temperature and humidity) will be appropriate for the test virus to obtain maximum survival following drying. The actual drying time and temperature will be recorded. Two carriers will be prepared for each lot of test agent and plate recovery control. Additionally, one carrier per test agent lot will be prepared for the neutralizer effectiveness control using cell culture media in place of stock virus.

C. Test agent preparation: The test agent will be prepared and used according to the Sponsor's directions or proposed label claims.

D. Test: For each of two batches of test substance, two dried virus films will be exposed to 2.0 ml of the use dilution of the test substance, or to the amount of spray released under use conditions (spray products) for a specified exposure time and temperature. Post contact time, the test agent will be neutralized and the mixture will be scraped from the surface of the dish. This will be considered approximately one $\log_{10}$ dilution.

1. Sephadex™/Sephacryl™ Filtration. If columns are utilized, each sample will be loaded into individual pre-spun Sephadex™/Sephacryl™ columns. Virus-test substance mixture will be passed through individual columns utilizing the syringe plunger or centrifugation in order to detoxify the mixture. The aseptically collected samples will be diluted as appropriate.

2. If columns are not used, serial tenfold dilutions of neutralized virus will be prepared in cell culture media. For spray-type agents, the agent will be used as per Sponsor's instructions, the volume produced by the spray product during the spraying application specified by the sponsor will be measured prior to testing and an equivalent quantity of the neutralizer will be applied post contact time. Following application of the test agent, contact time, and neutralization, the procedure for processing the samples will the same as described earlier (see above).

E. Infection, cell maintenance and infectivity assays: Selected dilutions of the neutralized inoculum/test agent mixture will be added to cultured cell monolayers. Four wells per dilution will be added to the host cell monolayers and incubated at 37±2° C. in 5±1% $CO_2$ for 5-7 days. Post incubation the infectious FCV will be scored microscopically by observing virus-specific cytopathic effects (CPE) produced by replicating infectious virus. The CPE associated with FCV is visually evidenced under the microscope by the presence of small, shrinking cells that have detached from the monolayer. These changes will be scored in comparison with the negative control (cell viability control).

F. Controls: All controls will be performed at the same time as the test, incubated under the same conditions and assayed in the same manner as the test (see above). Neutralizer effectiveness control, Cytotoxicity control and Cytotoxicity-related viral interference control will be performed for test agent(s).

1. Cell viability. control This control will demonstrate that cells remain viable throughout the course of the assay period. In addition, it will confirm sterility of the cell culture employed throughout the assay period. Four wells will receive cell culture media only.

2. Virus stock titer. The challenge virus will be titered at the time of the test to determine the relative infectivity of the virus and to demonstrate the susceptibility of the host cells to support infection of FCV. The virus inoculum will be serial diluted tenfold in cell culture media. Selected dilutions will be inoculated into four wells per dilution and incubated under the same conditions as the test.

3. Plate recovery control (PRC). Two ml of cell culture media will be added to the dried virus. Post-contact time, the virus/cell culture mixture will be subjected to the identical neutralization procedure as the test agent. If columns are used, a portion of the virus/cell culture media/neutralizer mixture will be used for the column titer control (see below). This control will determine the relative loss in virus infectivity resulting from drying and neutralization alone. The results from the PRC will be compared with the test results to confirm recovery of at least four $\log_{10}$ of infectious virus following drying and neutralization. Its titer will be used to compare with the titers of the test results to reach the acceptable test criteria (see below).

4. Neutralizer effectiveness control (NEC). The neutralization procedure will be dependent upon the active ingredient present in the test agent and in the internal control test agent. For this control, each lot of the test agent will be processed exactly as the test procedure, but instead of the viral inoculum, cell culture media will be added. Post neutralization, the sample will be divided into three portions [two for cytotoxicity related controls (see below) and one for neutralizer effectiveness].

If columns are used, each sample will be passed through individual columns and the eluate will be serial diluted as appropriate in cell culture media. If columns are not used, the neutralizer effectiveness samples will be serial diluted tenfold in cell culture media. The diluted samples will be mixed with low titer virus, held for a period equivalent to contact time and assayed for viral infectivity and/or cytotoxicity (see below), in order to determine the dilution of test agent at which virucidal activity, if any, is retained. Then the selected dilutions will be used to inoculate host cells as described for the test procedure. Dilutions that show virucidal activity will not be considered in determining reduction of viral infectivity by the test agent.

5. Cytotoxicity control (CT). A CT control will be run to determine if the product is toxic to the cells. Each lot of the neutralized test agent will be run to determine cytotoxicity. The CT sample, acquired from the NEC, will be serial diluted tenfold in cell culture media, having no virus added. Selected dilutions will be inoculated and incubated in the same manner as the test and control samples.

G. Calculations. Viral and cytotoxicity titers will be expressed as $-\log_{10}$ of the 50 percent titration endpoint infectivity ($TCID_{50}$), respectively, as calculated by the method of Spearman Karber.

$$-\text{Log of } 1^{st} \text{ dilution inoculated}-[(\text{Sum of \% mortality at each dilution}/100)-0.5)\times(\text{logarithm of dilution})]$$

The $\log_{10}$ reduction in infectivity will be calculated using the revised EPA approved method for calculating the Most Probable Number (MPN) as obtained from the EPA on Jan. 4, 2001.

Example 3: Testing of Efficacy in Different Environments and Against Multiple Pathogens The cleaning composition of the present application is tested for effectiveness according to EPA standard operating procedures to measure the effectiveness of hard surface disinfectants against *Staphylococcus aureus, Pseudomonas aeruginosa, Salmonella choleraesuis, Mycobacterium bovis, Clostridium difficile*, and viruses. The standard operating procedures are based on strict interpretations of AOAC International and ASTM International standard methods.

In an exemplary test, the cleaning composition of the present application is tested as a germicidal spray product with testing for effectiveness against *Staphylococcus aureus, Pseudomonas aeruginosa* and *Salmonella enterica* (EPA Method ID: MB-06-08 dated Sep. 22, 2014).

Test cultures of the bacterium are prepared as follows: Defrost a single cryovial at room temperature and briefly vortex to mix. Add 10 μL of the thawed frozen stock (single use) to a tube containing 10 mL of culture medium (Synthetic broth is used for *S. aureus, P. aeruginosa* and *S. enterica*. Nutrient broth may be used for *P. aeruginosa*.). Vortex, and incubate at 36±1° C. for 24±2 h. One daily transfer is required prior to the inoculation of a final test culture. Daily cultures may be subcultured for up to 5 days; each daily culture may be used to generate a test culture. For *S. aureus* and *S. enterica* only, briefly vortex the 24 h cultures prior to transfer. For the final subculture transfer, inoculate a sufficient number of 20×150 mm tubes containing 10 mL growth medium (e.g., synthetic broth or nutrient broth) with 10 μL per tube of the 24 h culture then vortex to mix. Incubate 48-54 h at 36±1° C. without shaking.

Carrier inoculation is carried out as follows: Inoculate approximately 80 carriers; 60 carriers are required for testing, 6 for control carrier counts, and 1 for the viability control. For *P. aeruginosa*, remove the pellicle from the broth either by decanting the liquid aseptically into a sterile tube, by gently aspirating the broth away from the pellicle using a pipette, or by vacuum removal. Avoid harvesting pellicle from the bottom of the tube. Transfer test culture after pellicle removal into sterile 25×150 mm test tubes (up to approximately 20 mL per tube) and visually inspect for pellicle fragments. Presence of pellicle in the final culture makes it unusable for testing.

For *S. aureus* and *S. enterica*, using a vortex-style mixer, mix 48-54 h test cultures 3-4 s and let stand 10 min at room temperature before continuing. Remove the upper portion of each culture (e.g., upper ¾ or approximately 7.5 mL), leaving behind any debris or clumps, and transfer to a sterile flask; pool cultures in the flask and swirl to mix.

For *S. aureus, P. aeruginosa* and *S. enterica*, using a vortex-style mixer, mix 48-54 h test cultures 3-4 s and let stand 10 min at room temperature before continuing. Remove the upper portion of each culture (e.g., upper ¾ or approximately 7.5 mL), leaving behind any debris or clumps, and pool culture into a sterile flask; swirl to mix. Measure and record the OD at 650 nm. Use sterile broth medium to calibrate the spectrophotometer. Note: To achieve mean carrier counts within the appropriate range (see section 8), the final test culture may be diluted (e.g., one part culture plus one part sterile broth) prior to the addition of the OSL to the inoculum using the sterile culture medium used to generate the final test culture (e.g., synthetic broth). Use the diluted test culture for carrier inoculation within 30 min. Add appropriate amount of organic burden if required. Swirl to mix.

Vortex-mix the inoculum periodically during the inoculation of carriers. Use a calibrated positive displacement pipette to transfer 0.01 mL of the culture to the sterile test carrier in the Petri dish. Immediately spread the inoculum uniformly using a sterile loop. Do not allow the inoculum to contact the edge of the glass slide carriers. Cover dish immediately. Dry carriers in incubator at 36±1° C. for 30-40 min. Perform efficacy testing within two hours of drying.

Enumeration of viable bacteria from carriers (control carrier counts) is conducted as follows: Assay dried carriers in 2 sets of three carriers, one set immediately prior to conducting the efficacy test and one set immediately following the test. Randomly select 6 inoculated carriers for carrier count analysis prior to efficacy testing. Place each of the inoculated, dried carriers in a 38×100 mm culture tube or sterile 50 mL polypropylene conical tube containing 20 mL of letheen broth. Vortex immediately—60±5 seconds for *P. aeruginosa* or 120±5 seconds for *S. aureus* and *S. enterica*. After vortexing, briefly mix and make serial tenfold dilutions in 9 mL dilution blanks of PBDW. Briefly vortex and plate 0.1 mL aliquots of appropriate dilutions in duplicate on TSA or BAP using spread plating. Plate appropriate dilutions to achieve colony counts in the range of 30-300 colony forming units (CFU) per plate. Spread inoculum evenly over the surface of the agar. Plates must be dry prior to incubation. If the serial dilutions are not made and plated immediately, keep the tubes at 2-5° C. until this step can be done. Complete the dilutions and plating within 2 h after vortexing. Alternatively, pool the letheen broth from the tubes with the carriers and briefly vortex. Serially dilute and plate 0.1 mL aliquots of the pooled media (60 mL). The average carrier count per set will be calculated. Incubate plates (inverted) at 36±1° C. for up to 48±2 h. Count colonies.

Disinfectant sample preparation is conducted as follows: For aerosol cans and trigger or pump sprayers, shake the can 25 times prior to use, unless otherwise specified by the manufacturer. Spray the test substance for 10-15 seconds prior to testing to ensure sprayer is operating correctly and test substance is dispensed properly. For concentrated test substances, aseptically prepare the test substance use-dilution required for the test using appropriate sterile glassware or pipettes. For concentrated test substances, use≥1.0 mL or 1.0 g of the test substance sample to prepare the final solution to be tested. Use v/v dilutions for liquid test substances and w/v dilutions for solids. Prior to testing, wipe the spray nozzle using 70% ethanol and sterile gauze and allow to dry.

The test procedure is conducted as follows: After the required carrier drying time, spray the slides sequentially for a specified time, distance, and number of pumps at timed intervals (typically 30 seconds) with the carriers in a horizontal position. Use a certified timer to time the spray interval. Spray the slide within ±5 seconds of the specified time for a contact time of 1-10 minutes or within ±3 seconds for contact times<1 minute. After spraying, maintain the carriers in a horizontal position. Treated carriers must be kept undisturbed during the contact time. After the last slide of a set (typically 20 slides) has been sprayed with the disinfectant, and the exposure time is complete, sequentially transfer each slide into the primary subculture tube containing the appropriate neutralizer within the ±5 second time limit. Drain the excess disinfectant from each slide prior to transfer into the neutralizer tube. Drain carriers without touching the Petri dish or filter paper. Perform transfers with flame sterilized or autoclaved forceps. The slide can touch both the interior sides of the Petri dish and the subculture tube during the transfer, but avoid this contact as much as possible. After the slide is deposited, recap the subculture tube and shake culture thoroughly. Incubate at 36±1° C. for 48±2 h.

Results are recorded as follows: Gently shake each tube prior to recording results. Record results as + (growth) or 0 (no growth) as determined by presence or absence of turbidity. Confirm a minimum of three positive carrier sets per test. If there are less than three positive carriers, then confirm each carrier.

The cleaning composition of the present application is tested against the parameters set by the EPA in the Series 810—Product Performance Test Guidelines, specifically public health uses of disinfectants (OCSPP 810.2200 (EPA-HQ-OPPT-2009-0150-0029)). To demonstrate efficacy, testing is conducted against *Salmonella enterica* (*S. enterica*), formerly designated as *Salmonella choleraesuis*, American Type Culture Collection (ATCC) 10708 for effectiveness against Gram-negative bacteria, or *Staphylococcus aureus* (*S. aureus*) (ATCC 6538) for effectiveness against Gram-positive bacteria. Three batches of the product are tested at the lower certified limit (LCL). For each batch, sixty carriers are used in the test. Three independent tests (i.e., three batches tested once on three different test days) are conducted against the test microbe at the LCL. The performance standard for *S. aureus* is 0-3 positive carriers out of sixty. The performance standard for *S. enterica* is 0-1 positive carriers out of sixty. Contamination of one carrier (culture tube) is allowed per 60-carrier set; occurrence of more than one contaminated carrier invalidates the test results. For germicidal spray products, the product should kill the test microorganisms on 59 out of each set of 60 carriers/slides. Contamination of only one carrier (culture tube) is allowed per 60-carrier set; occurrence of more than one contaminated carrier invalidates the test results.

For use as a hospital or healthcare disinfectant, to demonstrate efficacy, testing is conducted against *S. aureus* (ATCC 6538) and *Pseudomonas aeruginosa* (ATCC 15442). For use against fungus, to demonstrate efficacy, testing is conducted against *Trichophyton mentagrophytes* (ATCC 9533). For use against viruses, testing is conducted against Hepatitis B virus, Hepatitis C virus, and Norovirus, the Duck Hepatitis B virus, Bovine Viral Diarrhea virus, and Feline Calicivirus, respectively, which are considered acceptable surrogates for testing.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the object of the present application, and it is not intended to detail all those obvious modifications and variations of it which will become apparent to the skilled worker upon reading the description. It is intended, however, that all such obvious modifications and variations be included within the scope of the present application, which is defined by the following claims. The aspects and embodiments are intended to cover the components and steps in any sequence, which is effective to meet the objectives there intended, unless the context specifically indicates the contrary.

What is claimed is:

1. A method of formulating a cleaning composition, comprising the steps of:
   grinding an absorbent material to produce a granular absorbent material used in a coating step;
   coating the granular absorbent material with a coating agent to produce a coated absorbent material, wherein the coating agent is a biocide that forms a surface-bonded film on the granular absorbent material;
   adding a super-absorbent polymer to the coated absorbent material; and
   mixing the coated absorbent material with a sanitation agent, wherein the coated absorbent material absorbs the sanitation agent to form the cleaning composition, wherein the granular absorbent material is not perlite, and
   wherein the cleaning composition is capable of absorbing liquid at a liquid loading of 25-30% by volume or 200-300% by mass addition, and further
   wherein the granular absorbent material comprises vermiculite.

2. The method of claim 1, wherein the granular absorbent material is coated with the coating agent by vapor deposition, pressure micro droplet spray or fuming or fogging nozzle.

3. The method of claim 2, wherein the coating agent is coated in an amount that constitutes 0.1 to 10% (w/w) of the cleaning composition.

4. The method of claim 1, wherein the sanitation agent is added in an amount that constitutes 0.1 to 10% (w/w) of the cleaning composition.

5. A method of formulating a cleaning composition, comprising the steps of:
   grinding an absorbent material to produce a granular absorbent material used in a coating step;
   coating the granular absorbent material with a coating agent to produce a coated absorbent material, wherein the coating agent is a biocide that forms a surface-bonded film on the granular absorbent material;
   adding a super-absorbent polymer to the coated absorbent material; and
   mixing the coated absorbent material with a sanitation agent, wherein the coated absorbent material absorbs the sanitation agent to form the cleaning composition, wherein the granular absorbent material is not perlite, and wherein the cleaning composition is capable of absorbing liquid at a liquid loading of 25-30% by volume or 200-300% by mass addition, and further wherein the granular absorbent material comprises vermiculite, and also wherein the granular absorbent material has a surface area per mass ratio up to 10,000 $m^2/g$.

6. The method of claim 5, wherein the granular absorbent material is coated with the coating agent by vapor deposition, pressure micro droplet spray or fuming or fogging nozzle.

7. The method of claim 6, wherein the coating agent is coated in an amount that constitutes 0.1 to 10% (w/w) of the cleaning composition.

* * * * *